United States Patent
Ghosh et al.

(10) Patent No.: US 12,367,392 B1
(45) Date of Patent: Jul. 22, 2025

(54) APPARATUS (AND/OR METHOD) OF TRAINING A MACHINE-LEARNING MODEL TO GENERATE DETERMINATIONS USING MISMATCHED-CHANNEL SIGNALS

(71) Applicant: Anumana, Inc., Cambridge, MA (US)

(72) Inventors: Shayan Ghosh, Bangalore (IN); Yash Gupta, Bengaluru (IN); Shashi Kant, Bengaluru (IN); Rakesh Barve, Bengaluru (IN); Uddeshya Upadhyay, Bengaluru (IN)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/648,250

(22) Filed: Apr. 26, 2024

(51) Int. Cl.
| | |
|---|---|
| *G06N 3/08* | (2023.01) |
| *A61B 5/282* | (2021.01) |
| *G16H 20/10* | (2018.01) |
| *A61B 5/00* | (2006.01) |

(52) U.S. Cl.
CPC ............. *G06N 3/08* (2013.01); *A61B 5/7264* (2013.01)

(58) Field of Classification Search
CPC ................................. G06N 3/08; A61B 5/7264
See application file for complete search history.

(56) References Cited

U.S. PATENT DOCUMENTS

| | | | |
|---|---|---|---|
| 2021/0121090 A1* | 4/2021 | Weinstein | A61B 5/257 |
| 2021/0326704 A1* | 10/2021 | George | G06N 3/04 |
| 2023/0028783 A1 | 1/2023 | Zimmerman et al. | |
| 2023/0225665 A1* | 7/2023 | Kamousi | A61B 5/7264 |
| 2023/0309895 A1 | 10/2023 | Grande et al. | |
| 2023/0368023 A1* | 11/2023 | Nierenberg | G06N 3/08 |
| 2024/0070251 A1* | 2/2024 | Maizels | G06V 20/50 |

OTHER PUBLICATIONS

Smith et al; The Reconstruction of a 12-Lead Electrocardiogram from a Reduced Lead Set Using a Focus Time-Delay Neural Network; Acta Cardiol Sin. Jan. 2021; 37(1): 47-57.

* cited by examiner

*Primary Examiner* — Brandon S Cole
(74) *Attorney, Agent, or Firm* — Caldwell Intellectual Property Law

(57) ABSTRACT

An apparatus (and/or method) for training machine-learning model to make determinations from mismatched channel signals, wherein the apparatus includes a processor and memory communicatively connected to the processor. The memory containing instructions configuring the processor to receive a first set of signals using a first number of channels, process the first set of signals to simulate a second set of signals from a second number of channels, train a signal conversion model using the first set of signals and the second set of signals, and output a set of converted signals having the first number of channels using the third set of signals and the trained signal conversion model.

20 Claims, 8 Drawing Sheets

APPARATUS (AND/OR METHOD) OF TRAINING A MACHINE-LEARNING MODEL TO GENERATE DETERMINATIONS USING MISMATCHED-CHANNEL SIGNALS

FIELD OF THE INVENTION

The present invention generally relates to the field of machine-learning and training models. In particular, the present invention is directed to an apparatus (and/or method) of training a machine-learning model to generate determinations using mismatched-channel signals.

BACKGROUND

Many diagnostic tools have a standard regarding the amount and placement of channels. This includes both electrocardiograms (ECGs) as well as echocardiograms (EEGs). The 12-lead ECG is the gold standard ECG method used by cardiologists. Whereas EEGs can implement the placement of up to 64 separate electrodes or channels. However, accurate placement is both difficult and time consuming, many times leading to incorrect interpretation. Machine-learning algorithms have historically aided in the interpretation process to minimize human error; however, the algorithms are generally built using data from the standard use diagnostic tools, such as the 12-lead ECG and/or an EEG placing up to 64 electrodes. Despite this, there are many ECGs and/or EEGs which do not use the standard configuration.

SUMMARY OF THE DISCLOSURE

In an aspect, an apparatus for training a machine-learning model to generate determinations using mismatched-channel signals is described. The apparatus includes at least a processor and a memory communicatively connected to the at least a processor, wherein the memory contains instructions configuring the at least a processor to receive a first set of signals including a first number of channels. The memory contains instructions further configuring the at least a processor to process the first set of signals to simulate a second set of signals from a second number of channels that is distinct from the first number of channels, wherein processing the first set of signals includes filtering the first set of signals as a function of a preconfigured channel variation and transforming the filtered first set of signals into the second set of signals. The memory contains instructions further configuring the at least a processor to train a signal conversion model using the filtered and transformed first set of signals and the second set of signals. The memory contains instructions further configuring the at least a processor to receive a third set of signals having the second number of channels. The memory contains instructions further configuring the at least a processor to output a set of converted signals having the first number of channels using the third set of signals and the trained signal conversion model.

A method for training a machine-learning model to generate determinations using mismatched-channel signals is described. The method includes receiving, using at least a processor, a first set of signals including a first number of channels. The method further includes processing, using the at least a processor, the first set of signals to simulate a second set of signals from a second number of channels that is distinct from the first number of channels, wherein processing the first set of signals includes filtering the first set of signals as a function of a preconfigured channel variation and transforming the filtered first set of signals into the second set of signals. The method further includes training, using the at least a processor, a signal conversion model using the filtered and transformed first set of signals and the second set of signals. The method further includes receiving, using the at least a processor, a third set of signals having the second number of channels. The method further includes outputting, using the at least a processor, a set of converted signals having the first number of channels using the third set of signals and the trained signal conversion model.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatuses and methods for training a machine-learning model to generate determinations using mismatched-channel signals. In an embodiment, a method for training a machine-learning model to generate determinations using mismatched-channel signals may filter and process 6-lead ECG data to generate data similar to a 12-lead ECG.

Aspects of the present disclosure can be used to train a neural network, or similarly machine-learning models, to convert signal data between the different channel configurations. Aspects of the present disclosure can also be used to generalize the process for other embodiments of similar diagnostic tools, as an example and without limitation, in the case of ECGs, 1-lead ECG, 2-lead ECG, and the like. This is so, at least in part, because once the model has been trained, it can easily be used to convert between channel configurations regardless of the type of channel configuration data being entered.

Aspects of the present disclosure allow for the automatic conversion between mismatched-channel configurations. Exemplary embodiments illustrating aspects of the present disclosure are described below in the context of several specific examples.

Figure 1A:
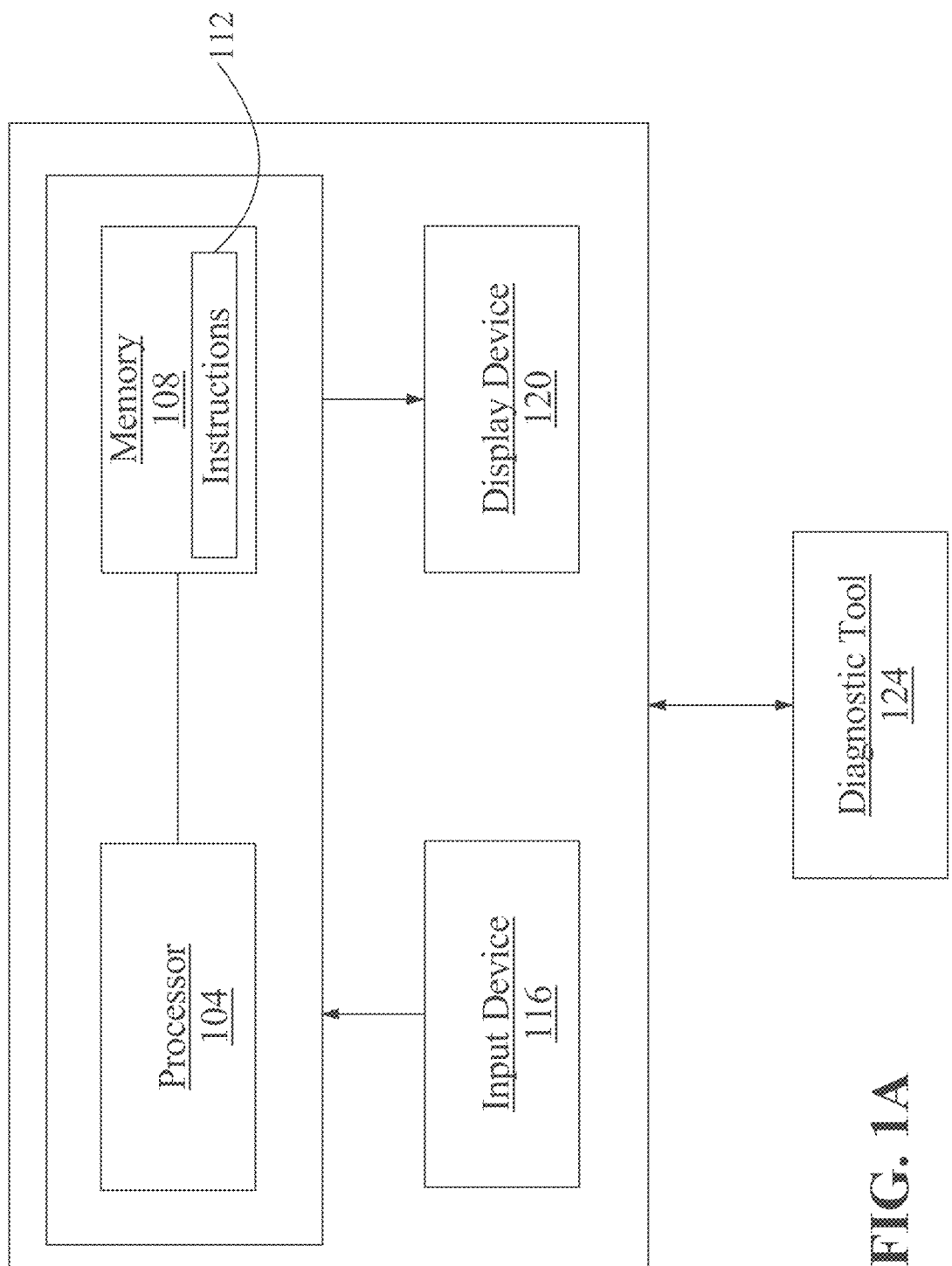
FIG. 1A is a block diagram illustrating an exemplary embodiment of an apparatus for training a machine learning model to generate determinations using mismatched-channel signals.

Referring now to FIG. 1A, an exemplary embodiment of an apparatus 100 (and/or method) for training a machine-learning model to generate determinations from mismatched-channel signals is illustrated. In an embodiment, an apparatus 100 (and/or method) for training machine-learning model to generate determinations from mismatched-channel signals includes at least a processor 104 and a memory 108 communicatively connected to the least a processor 104, wherein the memory 108 contains instructions 112 configuring the processor 104 to follow the method of training and implementing a machine-learning model to generate determinations using mismatched-channel signal. The method may include receiving a first set of signals using a number of channels, processing the first set of signals to simulate a second set of signals from a second number of channels, training a signal conversion model using the first set of signals and the second set of signals, receiving a third set of signals having the second number of channels, and outputting a set of converted signals having the first number of channels using the third set of signals and the trained signal conversion model. A "channel," as used in this disclosure, is a distinct medium, mechanism, and/or pathway by which a signal can travel. Two distinct channels may include, for instance, two distinct data paths for signals, such as two signals received from and/or via two sensors or leads, signals received via two distinct wires, signals received by two distinct antenna, two distinct frequency ranges such as corresponding to two distinct passbands in radiofrequency communication, two distinct "tracks" in an audio or other data recording, or the like. For example, and without limitation a channel may include a lead and/or an electrode in reference to ECGs and/or EEGs. As used in this disclosure, a "signal" is any intelligible representation of data, for example from one device to another. A signal may include an optical signal, a hydraulic signal, a pneumatic signal, a mechanical, signal, an electric signal, a digital signal, an analog signal and/or the like. In some cases, a signal may be used to communicate with a computing device, for example by way of one or more ports. In some cases, a signal may be transmitted and/or received by a computing device, for example, by way of an input/output port. An analog signal may be digitized, for example by way of an analog to digital converter. In some cases, an analog signal may be processed, for example by way of any analog signal processing steps described in this disclosure, prior to digitization. In some cases, a digital signal may be used to communicate between two or more devices, including without limitation computing devices. In some cases, a digital signal may be communicated by way of one or more communication protocols, including without limitation internet protocol (IP), controller area network (CAN) protocols, serial communication protocols (e.g., universal asynchronous receiver-transmitter (UART)), parallel communication protocols (e.g., printer port), and the like.

Still referring to FIG. 1A, in some cases, apparatus 100 (and/or method) may perform one or more signal processing steps on a signal. For instance, apparatus 100 may analyze, modify, and/or synthesize a signal representative of data in order to improve the signal, for instance by improving transmission, storage efficiency, or signal to noise ratio. Exemplary methods of signal processing may include analog, continuous time, discrete, digital, nonlinear, and statistical. Analog signal processing may be performed on non-digitized or analog signals. Exemplary analog processes may include passive filters, active filters, additive mixers, integrators, delay lines, compandors, multipliers, voltage-controlled filters, voltage-controlled oscillators, and phase-locked loops. Continuous-time signal processing may be used, in some cases, to process signals which vary continuously within a domain, for instance time. Exemplary non-limiting continuous time processes may include time domain processing, frequency domain processing (Fourier transform), and complex frequency domain processing. Discrete time signal processing may be used when a signal is sampled non-continuously or at discrete time intervals (i.e., quantized in time). Analog discrete-time signal processing may process a signal using the following exemplary circuits sample and hold circuits, analog time-division multiplexers, analog delay lines and analog feedback shift registers. Digital signal processing may be used to process digitized discrete-time sampled signals. Commonly, digital signal processing may be performed by a computing device or other specialized digital circuits, such as without limitation an application specific integrated circuit (ASIC), a field-programmable gate array (FPGA), or a specialized digital signal processor (DSP). Digital signal processing may be used to perform any combination of typical arithmetical operations, including fixed-point and floating-point, real-valued and complex-valued, multiplication and addition. Digital signal processing may additionally operate circular buffers and lookup tables. Further non-limiting examples of algorithms that may be performed according to digital signal processing techniques include fast Fourier transform (FFT), finite impulse response (FIR) filter, infinite impulse response (IIR) filter, and adaptive filters such as the Wiener and Kalman filters. Statistical signal processing may be used to process a signal as a random function (i.e., a stochastic process), utilizing statistical properties. For instance, in some embodiments, a signal may be modeled with a probability distribution indicating noise, which then may be used to reduce noise in a processed signal.

Continuing to reference FIG. 1A, in an embodiment, a channel signal may include an electrocardiogram (ECG) reading. An ECG is a medical assessment of cardiovascular disease. The standard embodiment of ECG is a 12-lead ECG, however additional embodiments with fewer leads exist, such as, without limitation, 6-lead ECGs like the AliveCor 6-lead ECG. ECGs are able to assess cardiac rhythm, detection of myocardial ischemia and infarction, conduction system abnormalities, preexcitation, long QT syndromes, atrial abnormalities, ventricular hypertrophy, pericarditis, and/or other similar conditions. As used in this disclosure, "ECG reading" and or "ECG data," refer to the electrical signal recorded from a patient's heart by placing electrodes on the patient's body. The signals of a patient's heart are shown as waves, which can then be read to indicate potential and current issues with the rhythm of their heart which may implicate certain medical diagnoses. A "first set of signals using a number of channels," as used in this disclosure, describes the configuration of the initial channel data collected by any given diagnostic tool 124. For example, and without limitation, a first set of signals using a number of channels may include set of signals from a standard 12-lead ECG. A 12-lead ECG is an ECG device that captures of electrical activity of a patient's heart from 12 different channels. Likewise, a 6-lead ECG would indicate 6 different channels, wherein the channels would provide individual signals associated with each channel. In some embodiments, first set of signals may include a first number of channels. A "lead," as used in this disclosure is one or more electrodes attached to the skin to detect a heart's electric signals. The first set of signals using a number of channels may additionally include any configuration of a diagnostic tool 124. As a nonlimiting example an ECG, may further include, but is not limited to 1-lead, 2-lead, and so on. As used in this disclosure, a "second number of channels," is a second channel configuration of a diagnostic device configured in a distinct manner than the first channel configuration. A second number of channels may include a reduced-channel configuration, wherein the reduced-channel configuration may include fewer channels than the first channel configuration. For example, and without limitation, a reduced-channel configuration of an ECG may include a 6-lead ECG: leads I, II, III, aVL, aVF, and aVR. Alternatively, a second number of channels may include an increased-channel configuration, wherein the configuration may include more channels than the first channel configuration. For example, and without limitation, first set of signals using a number of channels may include a 6-lead ECG while a second set of signals using a distinct number of channels from the first set of signals may include a 12-lead ECG.

With further reference to FIG. 1A, in an embodiment, a channel signal may include an echocardiogram reading (EEG). An EEG is a test that detects abnormalities in the brain waves and/or in the electrical activity of the brain. Throughout the procedure, electrodes are pasted onto the scalp of the patient. The electrodes detect small electrical charges that result from the activity of the brain. An EEG may be used to detect and/or help diagnose conditions such as seizures, epilepsy, head injuries, dizziness, headaches, brain tumors, and/or sleeping problems. Typically, a 10-20 system is used. The 10-20 system is a standardization of the method of EEG placement. The numbers "10 and "20" refer to the distances between adjacent electrodes, which are either 10% or 20% of the total distance (front-back or right-left) of the skull. As described above in relation to ECGs, EEGs similarly may be included as signals. Therefore, EEG readings may be represented as a set of signals as used throughout the process of training the machine-learning model as well as throughout the entirety of the process as described throughout the disclosure.

Continuing to reference FIG. 1A, in an embodiment, processing the first set signals to simulate a second set of signals from a second number of channels that is distinct from the first number of channels may include filtering the first set of signals as a function of a preconfigured channel variation. As used in this disclosure, "preconfigured channel variation," refers to the sought after signal configuration associated with a designated channel variation. For example, and without limitation, filtering of a 12-lead ECG as a function of a 6-lead ECG. This may include data that is related to a specific disease and/or medical condition. Furthermore, configured channel variations may be selected and extracted from corresponding diagnostic tool 124 readings. Signal processing techniques may be applied to the signals to replicate the characteristics of lower-channel configuration. For example, and without limitation, by filtering out certain frequencies or signal components that are not typically captured under the second channel configuration, one is left with anomalies that are present in both the increased-channel configuration signals and the lower-channel configuration signals. This may be accomplished by isolating one or more signals corresponding to the preconfigured channel variation from the first set of signals using a digital signal processing algorithm. Exemplary, nonlimiting signal processing techniques may include wavelet transforms, Fourier analysis, band-pass filtering, and/or the like and may either enhance or isolate signals. Wavelet transforms include two broad classes: the continuous wavelet transform (CWT) and the discrete wavelet transform (DWT). CWT is a time-frequency transform, which is ideal for analysis of non-stationary signals such as the signals introduced by the first set of signals having a number of channels. CWT is similar to the short-time Fourier transform (STFT), which uses a fixed window to create a local frequency analysis, while CWT tiles the time-frequency plane with variable-sized windows. The window widens in time, making it suitable for low-frequency phenomena, and narrows for high-frequency phenomena. The CWT can be used to analyze transient behavior, rapidly changing frequencies, and slowly varying behavior. Band-pass filtering selectively filters out unwanted frequencies and isolates a desired signal. For instance, in an embodiment using ECG data as signals, band-pass filtering may only allow specific frequencies to pass through, such as those frequencies associated with a lower and/or higher channel configuration.

With further reference to FIG. 1A, in an embodiment, processing the first set of signals to simulate a second set of signals from a second number of channels that is distinct from the first number of channels may further include transforming the filtered first set of signals into the second set of signals. In some embodiments, when transforming to configurations with fewer channels, data reduction techniques may be applied to first set of signals to select channels that provide the most significant information about a patient's condition. For example, and without limitation, when signals include ECG data, lead I and lead II, for a 2-lead configuration, may be especially important. In some embodiments, second set of signals may include one or more synthetic data points generated using generative and/or data augmentation algorithms. For example, and without limitation, in the case of increased-channel configuration, generative adversarial network (GAN) may replace missing channels with synthetic data points. In some embodiments, one or more machine-learning models may be employed to learn transformation patterns from the signals received through the first number of channels.

Further referencing FIG. 1A, in an embodiment where the second set of signals having a number of channels distinct from the first set of signals includes an increased-channel configuration, processing of the first set of signals may further include: generating one or more synthetic signals as a function of the first set of signals to simulate one or more additional channels not presented in the first channel configuration, and generating the second set of signals representative of the increased-channel configuration by integrating the synthetic signals with the first set of signals. This may be accomplished through interpolation via generative AI.

Continuing to reference FIG. 1A, in some embodiments, an apparatus 100 (and/or method) for training machine-learning model to generate determinations from mismatched-channel signals may further include instructions 112 configuring the at least a processor 104 to generate a visual representation of the converted signal set having the first number of channels using the third set of signals and the trained signal conversion model, and display the visual representation of the set of converted signals alongside a visual representation of the first set of signals using a visual interface at display device 120. A visual representation may include waves displayed on a graph indicating electrical impulses recorded and/or simulated by a diagnostic device. This visual representation may include the converted signal set having the first number of channels on their own or in tandem with the first set of signals. These visual representations may be displayed on any display device 120 as described within this disclosure and discussed in further detail below.

Further referencing FIG. 1A, in some embodiments, one or more components of the method of processing the first set of signals to simulate a second set of signals from a second channel configuration distinct from the first set of signals having a number of channels may be improved and/or fine-tuned by using aggregations, instantiating a machine-learning model, and/or instantiating a neural network. Training data that may be used to train the machine-learning model and/or the neural network may include exemplary and nonlimiting input data, such as, first set of signals, second set of signals, known electrical anomalies associated with desired channel configurations, signals of desired channel configurations, predictions of signals of desired channel configurations, and the like, where each such example may be correlated to additional exemplary output data such as, without limitation, first set of signals, second set of signals, known electrical anomalies associated with desired channel configurations, signals of desired channel configurations, predictions of signals of desired channel configurations, and the like. Training of the model/network may take place either at apparatus 100 or remotely; in the latter case, the model/network may be deployed at or by apparatus 100 in any manner as described within this disclosure. Additionally, in some embodiments, the machine-learning model and/or the neural network may be updated to apparatus 100, the model/network may be deployed at or by apparatus 100 in any manner as described in this disclosure. The machine-learning model and/or neural network may be deployed/instantiated once trained in any form as described within this disclosure. Feedback from the deployment of the machine-learning model and/or neural network may be turned into new training data, which may be stored either locally and/or transmitted to another device and used for retraining of the model/network. Retraining may be administered either remotely or at apparatus 100. Following the retraining of the model/network, redeployment/instantiation may be accomplished at or by apparatus 100 in any manner as described within this disclosure.

Continuing to reference FIG. 1A, in an embodiment an apparatus 100 (and/or method) for training machine-learning model to make determinations from mismatched-channel signals, includes training a signal conversion model using the first set of ECG readings and the second set of ECG readings. By correlating the filtered signals and the second set of signals that mimic lower-channel configurations with the original signals, training data may be generated and used to train the signal conversion model to convert signals between different channel configurations. For example, and without limitation, signal conversion model may be able to take a signal from one type of machine, such as a 12-lead ECG and estimate what the corresponding 6-lead ECG would look like and vice-versa. Training data that may be used to train the signal conversion model may include exemplary input data, such as without limitation, a first set of signals, a second set of signals, a filtered first set of signals, known electrical anomalies associated with desired channel selections, signals of desired channel configurations, predictions of signals of desired channel selections, and/or the like, where each such example may be correlated to additional exemplary output data such as, without limitation, a first set of signals, a second set of signals, a filtered first set of signals, known electrical anomalies associated with desired channel configurations, signals of desired channel configurations, predictions of signals of desired channel configurations, and/or the like. Training of the signal conversion model may take place either at apparatus 100 and/or remotely; in the latter case, the model may be deployed at or by apparatus 100 in any manner as described within this disclosure. Additionally, in some embodiments, the signal conversion model may be updated to apparatus 100, the model may be deployed at or by apparatus 100 in any manner as described in this disclosure. The signal conversion model may be deployed/instantiated once trained in any form as described within this disclosure. Feedback from the deployment of the signal conversion model may be turned into new training data, which may be stored either locally and/or transmitted to another device and used for retraining of the model. Retraining may be administered either remotely or at apparatus 100. Following the retraining of the ECG reading conversion model, redeployment/instantiation may be accomplished at or by apparatus 100 in any manner as described within this disclosure.

Continuing to reference FIG. 1A, an apparatus 100 (and/or method) for training a machine-learning model to generate determinations using mismatched-channel signals includes receiving a third set of signals having the second number of channels. The third set of signals having the second number of channels may be received through manual user input at input device 116, by direct communicative connection to a specific diagnostic tool 124, and/or from a distinct machine-learning model that may be configured to detect one or more medical diagnoses. The latter may additionally constitute a diagnostic tool 124. The third set of signals having the second number of channels may include a second number of channels designated by a user. Without limitation, the first number of channels may exceed the first number of channels. Alternatively, and without limitation, the third set of signals may include a second number of channels that is lower than the first number of channels. Signals received may be in any embodiment as discussed within this disclosure.

With further reference to FIG. 1A, an apparatus 100 (and/or method) for training a machine-learning model to generate determinations from mismatched-channel signals includes outputting a set of converted signals in a target channel configuration using the third set of signals and the trained signal conversion model. As used in this disclosure, a "target channel configuration" is a specified configuration received by the conversion model and relates to the third set of signals. In some embodiments the target lead configuration may be specified by the user. Additionally, and alternatively, the target lead configuration may be specified by other machine-learning models; for example, machine-learning models that take in ECG readings and detect specific medical issues. In an embodiment, outputting a set of converted signal set may additionally include outputting the set of converted signals into an additional machine-learning model, wherein the additional machine-learning model is trained to perform one or more specific diagnostic tasks using signals in the target channel configuration as input. Specific and nonlimiting diagnostic tasks may include cardiac condition diagnosis. For example, and without limitation, a fast, slow, or abnormal heart rhythm, a heart defect, coronary artery disease, hyperkalemia, pulmonary heart disease, heart valve disease, an enlarged heart, and/or signs of a past or near future heart attack. This machine-learning model may be consistent with disease model 148 in FIG. 1B.

With continued reference to FIG. 1A, an apparatus 100 (and/or method) for training a machine-learning model to generate determinations from mismatched-channel signals may include a computing device. Computing device includes a processor communicatively connected to memory 108, wherein memory 108 contains instructions 112 configuring the at least a processor to receive a first set of signals using a number of channels, process the first set of signals to simulate a second set of signals from a second number of channels that is distinct from the first number of channels, train a signal conversion model using the first set of signals and the second set of signals, receive a third set of signals having the second number of channels, and output a set of converted signals set having the first number of channels using the third set of signals and the trained signal conversion model. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Further referring to FIG. 1A, Computing device may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device may include a single computing device operating independently, or may include two or more computing device operating in concert, in parallel, sequentially or the like; two or more computing devices may be included together in a single computing device or in two or more computing devices. Computing device may interface or communicate with one or more additional devices as described below in further detail via a network interface device. Network interface device may be utilized for connecting computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device may include but is not limited to, for example, a computing device or cluster of computing devices in a first location and a second computing device or cluster of computing devices in a second location. Computing device may include one or more computing devices dedicated to data storage, security, distribution of traffic for load balancing, and the like. Computing device may distribute one or more computing tasks as described below across a plurality of computing devices of computing device, which may operate in parallel, in series, redundantly, or in any other manner used for distribution of tasks or memory between computing devices. Computing device may be implemented, as a non-limiting example, using a "shared nothing" architecture.

With continued reference to FIG. 1A, computing device may be designed and/or configured to perform any method, method step, or sequence of method steps in any embodiment described in this disclosure, in any order and with any degree of repetition. For instance, computing device may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Figure 1B:
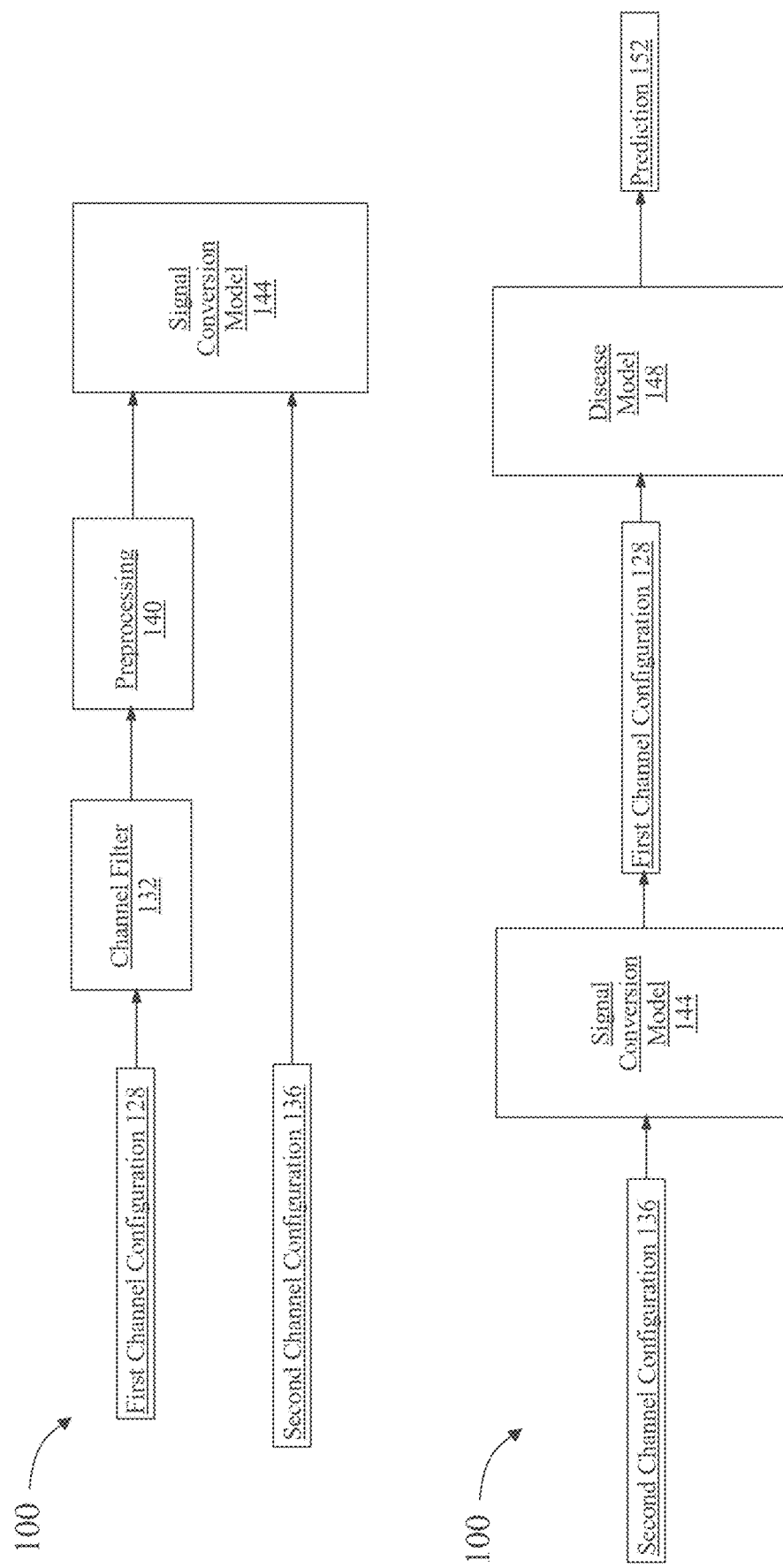
FIG. 1B is a block diagram illustrating an exemplary embodiment of the apparatus for training a machine learning model to generate determinations using mismatched-channel signals.

Referring now to FIG. 1B, apparatus 100 is shown in another embodiment. Apparatus 100 may receive a first set of signals in a first channel configuration 128. First channel configuration 128 may include a particular number of channels, a particular lead configuration, or the like. In some embodiments, first channel configuration 128 may include a 12 lead and/or channel ECG. In some embodiments, first channel configuration 128 may include an ECG with greater than 12 leads. In some embodiments, first channel configuration 128 may include an ECG with less than 12 leads. In some embodiments, first channel configuration 128 may include an ECG with 6 leads. In some embodiments, first channel configuration 128 may include an ECG with 16 leads. In some embodiments, first channel configuration 128 may include an ECG with 2 leads. In some embodiments, first channel configuration 128 may include an ECG with 1 lead.

With continued reference to FIG. 1B, signals in first channel configuration 128 may be filtered using channel filter 132. Channel filter 132 may perform any filtering steps disclosed throughout this disclosure. In some embodiments, filtering may include extracting signals corresponding to certain leads from the first set of signals. Signal processing techniques may be applied to first set of signals such that they replicate the characteristics of signals in a second channel configuration 136 (second channel configuration 136 may have a greater or lesser number of channels/leads). As a non-limiting example, channel filter 132 may filter out frequencies that are not typically captured for signals in second channel configuration 136. As a non-limiting example, channel filter 132 may filter out certain signal components that are not typically captured for signals in second channel configuration 136. Exemplary signal processing techniques may include, without limitation, wavelet transforms, Fourier analysis, band-pass filtering, and/or the like, which may be used to isolate or enhance the signals.

With continued reference to FIG. 1B, signals may also be put through a preprocessing 140 step. Preprocessing 140 may include the generation of synthetic signals, which may be consistent with the generation of synthetic signals disclosed with reference to FIG. 1A. Preprocessing 140 may include wavelet transforms, Fourier analysis, band-pass filtering, and/or the like may be used to isolate or enhance ECG readings.

With continued reference to FIG. 1B, apparatus may include signal conversion model 144. Signal conversion model 144 may be consistent with any signal conversion model disclosed in this disclosure. Particularly, signal conversion model may be consistent with signal conversion model disclosed with reference to FIG. 1A. As disclosed above, signal conversion model 144 may be trained on training data comprising signals with first channel configuration 128 correlated to signals with second channel configuration 136. In some embodiments, signal conversion model 144 may be trained on training data comprising signals with first channel configuration 128 correlated to the signals with first channel configuration 128 that have been converted into second channel configuration 136.

With continued reference to FIG. 1B, signal conversion model 144 may receive signals, such as a third set of signals, in second channel configuration 136 as input and output the signals (third set of signals) in first channel configuration 128 as output. In some embodiments, these converted signals (third set of signals) in first channel configuration 128 may be received as input to a disease model 148. A "disease model," for the purposes of this disclosure is a mathematical model that is configured to make one or more prediction 152 using signals as input. In some embodiments, input to disease model 148 may be ECGs. Predictions may include Medical predictions, as non-limiting examples, may include the presence or absence (or likelihood or presence or absence) of a disease, a medical parameter of the health of an individual, and the like. Medical predictions may be related to hyperkalemia, pulmonary cardiac disease, coronary heart disease, ejection fraction, and the like. Disease model may be consistent with any disease model disclosed in this disclosure. In some embodiments, disease model 148 may include a machine-learning model. Disease model 148 may be trained with disease training data correlating signals to predictions. In some embodiments, disease model 148 may be trained with training data correlating ECG signals to medical predictions.

Figure 2:
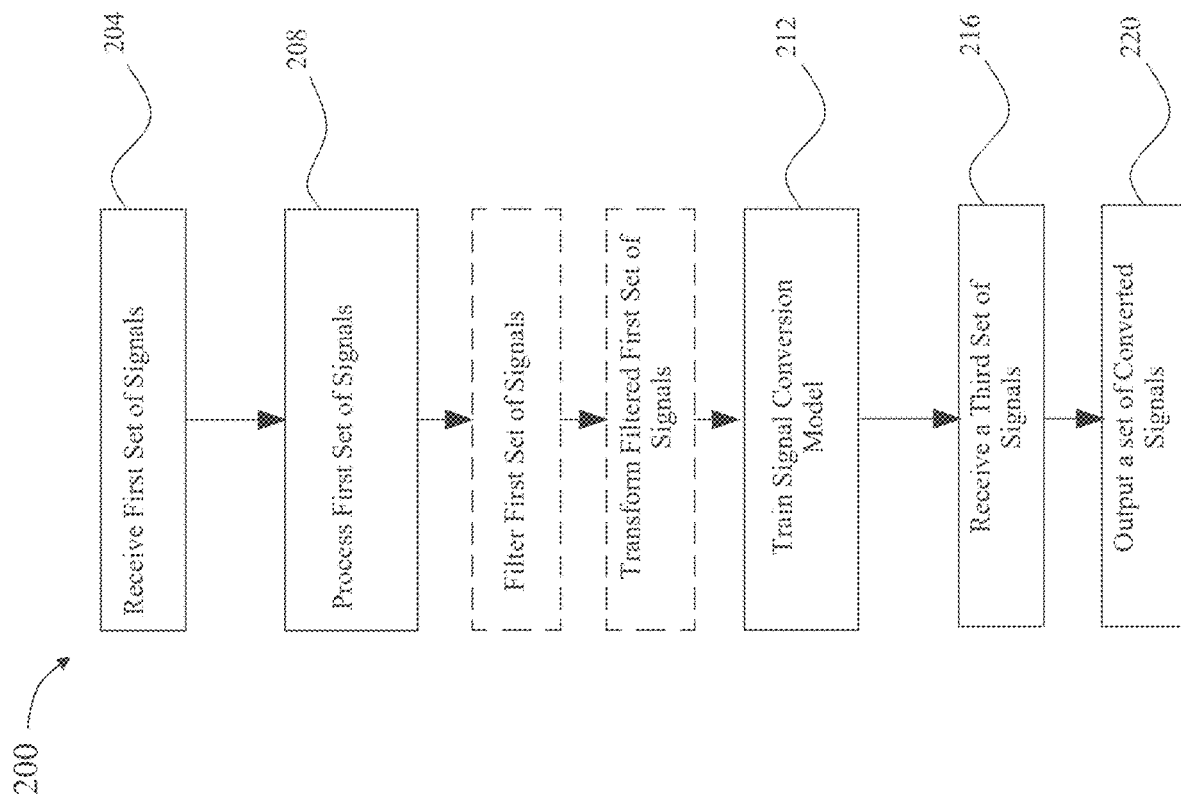
FIG. 2 is a flow diagram illustrating a method of training a machine learning model to generate determinations using mismatched-channel signals.

Now referring to FIG. 2, a flow diagram of a method 200 of training a machine learning model to generate determinations using mismatched-channel signals is shown. Method 200 is an exemplary embodiment of the instructions within the memory of apparatus for training a machine learning model to generate determinations using mismatched-channel signals. Method 200 may be implemented in any way as previously discussed in relation to FIGS. 1A and B above. Furthermore, embodiments of method 200 may include any variation as previously discussed in relation to FIGS. 1A and B above. As shown the exemplary nonlimiting embodiment of method 200 includes receiving a first set of signals 204. This may be implemented as described in any of FIGS. 1A-7. Method 200 further includes a step 208 of processing the first set of signals to simulate a second set of signals from a second number of channels that is distinct from the first number of channels. This may be implemented as described in any of FIGS. 1A-7. Method 200 includes a step 212 of training a signal conversion model using the first set of signals and the second set of signals. This may be implemented as described in any of FIGS. 1A-7. Method 200 includes a step 216 of receiving a third set of signals having the second number of channels. This may be implemented as described in any of FIGS. 1A-7. Method 200 includes a step 220 of outputting a set of converted signals having the first number of channels using the third set of signals and the trained signal conversion model. This may be implemented as described in any of FIGS. 1A-7. In some embodiments, step 208 may include the steps of outputting the set of converted signals may include wherein processing the first set of signals further includes filtering the first set of signals as a function of a preconfigured channel variation and transforming the filtered first set of signals into the second set of signals. This may be implemented as described in any of FIGS. 1A-7.

Figure 3:
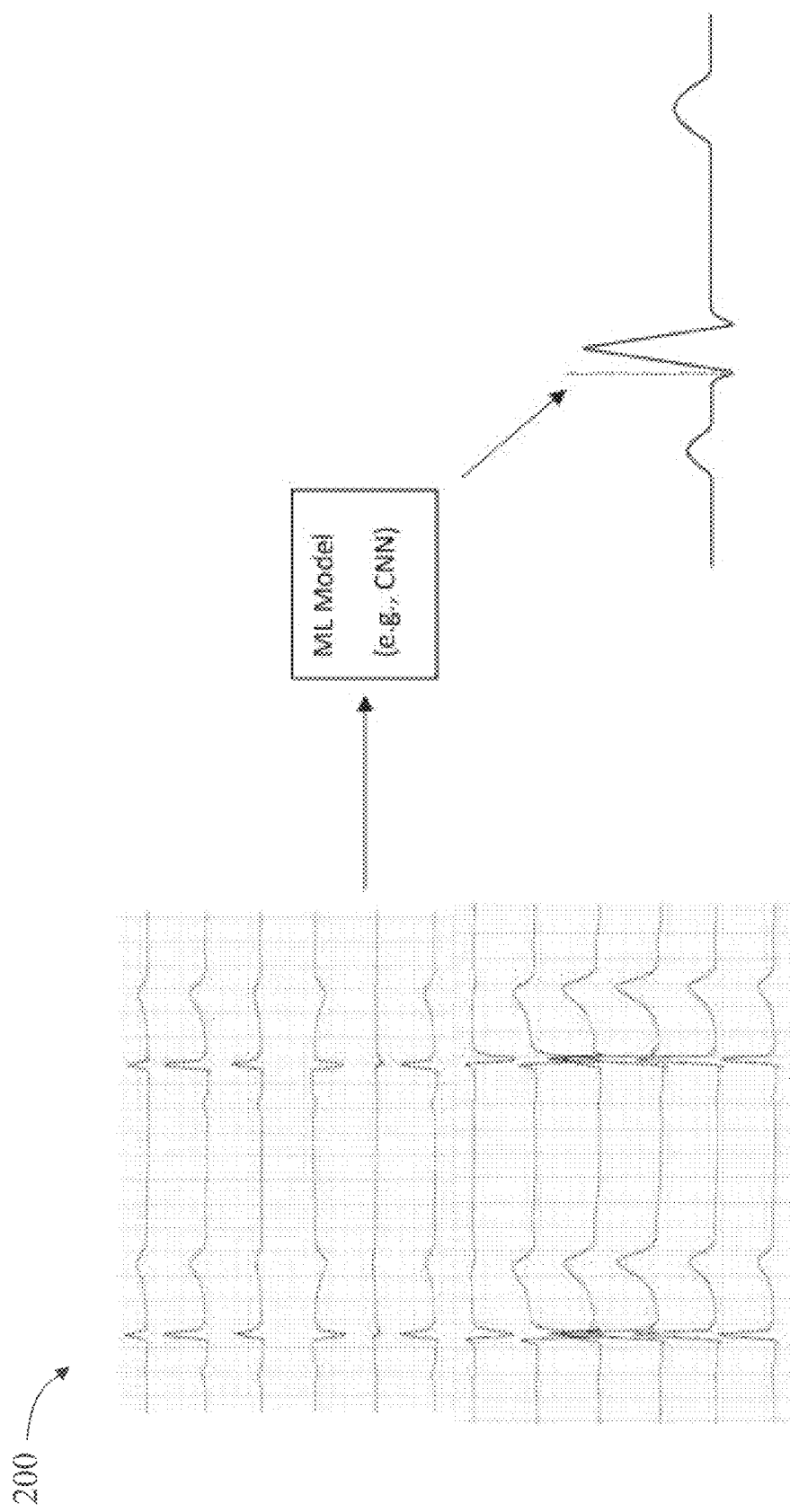
FIG. 3 illustrates particular implementations of various steps of a method of training a machine learning model to generate determinations using mismatched-channel signals.

Now referring to FIG. 3, an exemplary embodiment of particular implementations of various steps of a method of training a machine learning model to generate determinations using mismatched-channel signals. In an embodiment, 12-lead ECG reading data may be received and input into trained ECG reading conversion model outputting a set of converted ECG readings in a desired channel configuration based on the first set of ECG signals. As pictured, in FIG. 3, the first set of ECG readings are displayed in tandem with a converted ECG reading appearing in the desired target channel configuration of 1-lead.

Figure 4:
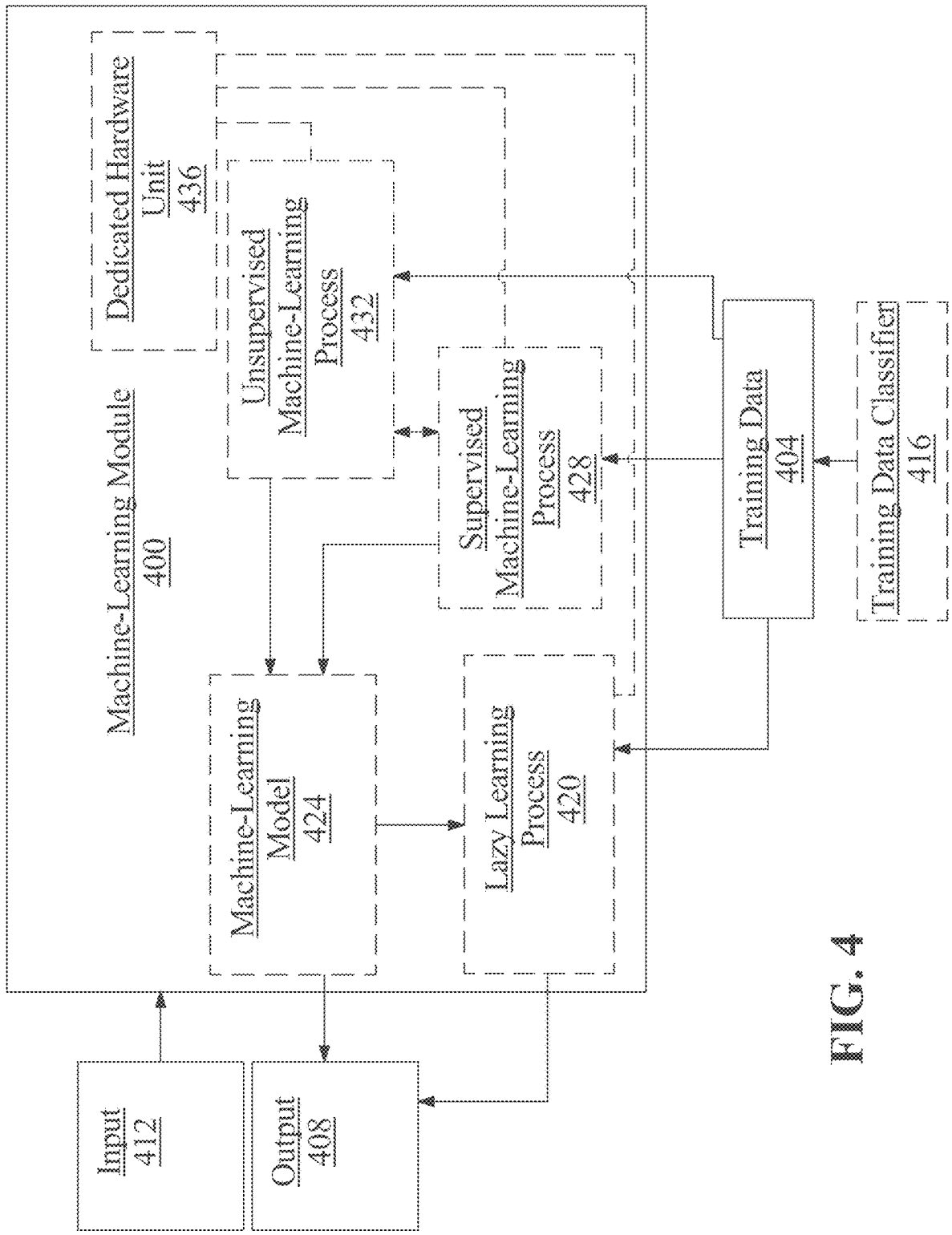
FIG. 4 is an exemplary machine-learning module.

Referring now to FIG. 4, an exemplary embodiment of a machine-learning module 400 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 404 to generate an algorithm instantiated in hardware or software logic, data structures, and/or functions that will be performed by a computing device/module to produce outputs 408 given data provided as inputs 412; this is in contrast to a non-machine learning software program where the commands to be executed are determined in advance by a user and written in a programming language.

Still referring to FIG. 4, "training data," as used herein, is data containing correlations that a machine-learning process may use to model relationships between two or more categories of data elements. For instance, and without limitation, training data 404 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 404 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 404 according to various correlations; correlations may indicate causative and/or predictive links between categories of data elements, which may be modeled as relationships such as mathematical relationships by machine-learning processes as described in further detail below. Training data 404 may be formatted and/or organized by categories of data elements, for instance by associating data elements with one or more descriptors corresponding to categories of data elements. As a non-limiting example, training data 404 may include data entered in standardized forms by persons or processes, such that entry of a given data element in a given field in a form may be mapped to one or more descriptors of categories. Elements in training data 404 may be linked to descriptors of categories by tags, tokens, or other data elements; for instance, and without limitation, training data 404 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 4, training data 404 may include one or more elements that are not categorized; that is, training data 404 may not be formatted or contain descriptors for some elements of data. Machine-learning algorithms and/or other processes may sort training data 404 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 404 to be made applicable for two or more distinct machine-learning algorithms as described in further detail below. Training data 404 used by machine-learning module 400 may correlate any input data as described in this disclosure to any output data as described in this disclosure. As a non-limiting illustrative example first set of ECG readings, second set of ECG readings, and or the like.

Further referring to FIG. 4, training data may be filtered, sorted, and/or selected using one or more supervised and/or unsupervised machine-learning processes and/or models as described in further detail below; such models may include without limitation a training data classifier 416. Training data classifier 416 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 400 may generate a classifier using a classification algorithm, defined as a processes whereby a computing device and/or any module and/or component operating thereon derives a classifier from training data 404. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 416 may classify elements of training data to characterize a sub-population based on signal readings correlated to specific diagnoses.

With continued reference to FIG. 4, computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 4, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 4, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 4, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 4, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, santization may include utilizing algorithms for identifying duplicate entries or spell-check algorithms.

As a non-limiting example, and with further reference to FIG. 4, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 4, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 4, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 4, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 4, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $X_{max}$:

$$X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 4, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

With continued reference to FIG. 4, in one or more embodiments, computing device may implement one or more aspects of "generative artificial intelligence (AI)," a type of AI that uses machine learning algorithms to create, establish, or otherwise generate data such as, without limitation, a converted signal set having a first number of channels using the third set of signals and the trained signal conversion model and/or the like in any data structure as described herein (e.g., text, image, video, audio, among others) that is similar to one or more provided training examples. In an embodiment, machine learning module described herein may generate one or more generative machine learning models that are trained on one or more sets of data including without limitation, first sets of signals, second sets of signals from a second number of channels distinct from the first number of channels, a third set of signals having the second number of channels, a converted set of signals having the first number of channels, and/or the like. One or more generative machine learning models may be configured to generate new examples that are similar to the training data of the one or more generative machine learning models but are not exact replicas; for instance, and without limitation, data quality or attributes of the generated examples may bear a resemblance to the training data provided to one or more generative machine learning models, wherein the resemblance may pertain to underlying patterns, features, or structures found within the provided training data.

Still referring to FIG. 4, in some cases, generative machine learning models may include one or more generative models. As described herein, "generative models" refers to statistical models of the joint probability distribution P(X, Y) on a given observable variable x, representing features or data that can be directly measured or observed (e.g., a first set of signals and/or a second set of signals) and target variable y, representing the outcomes or labels that one or more generative models aims to predict or generate (e.g., a set of converted signals having the first number of channels). In some cases, generative models may rely on Bayes theorem to find joint probability; for instance, and without limitation, Naïve Bayes classifiers may be employed by computing device to categorize input data such as, without limitation, a first set of signals and/or a second set of signals having a distinct number of channels from the first set of signals into different classes, labels, cohorts, categories or the like such as, without limitation, specific channels.

In a non-limiting example, and still referring to FIG. 4, one or more generative machine learning models may include one or more Naïve Bayes classifiers generated, by computing device, using a Naïve bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A)\ P(A)\div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing Device may then calculate a likelihood table by calculating probabilities of different data entries and classification labels. Computing device may utilize a naïve Bayes equation to calculate a posterior probability for each class. A class containing the highest posterior probability is the outcome of prediction.

Still referring to FIG. 4, although Naïve Bayes classifier may be primarily known as a probabilistic classification algorithm; it may also be considered a generative model described herein due to its capability of modeling the joint probability distribution P(X, Y) over observable variables X and target variable Y. In an embodiment, Naïve Bayes classifier may be configured to make an assumption that the features X are conditionally independent given class label Y, allowing generative model to estimate the joint distribution as $P(X, Y)=P(Y)\Pi i P(X_i|Y)$, wherein $P(Y)$ may be the prior probability of the class, and $P(X_i|Y)$ is the conditional probability of each feature given the class. One or more generative machine learning models containing Naïve Bayes classifiers may be trained on labeled training data, estimating conditional probabilities $P(X_i|Y)$ and prior probabilities $P(Y)$ for each class; for instance, and without limitation, using techniques such as Maximum Likelihood Estimation (MLE). One or more generative machine learning models containing Naïve Bayes classifiers may select a class label y according to prior distribution $P(Y)$, and for each feature $X_i$, sample at least a value according to conditional distribution $P(X_i|y)$. Sampled feature values may then be combined to form one or more new data instance with selected class label y. In a non-limiting example, one or more generative machine learning models may include one or more Naïve Bayes classifiers to generate new examples of a converted signals set having the first number of channels based on a first set of signals using a number of channels and a second set of signals having a distinct number of channels from the first number of channels (e.g., 6-channel configuration, 12-channel configuration, and/or the like), wherein the models may be trained using training data containing a plurality of features e.g., features of a first set of signals having a number of channels and/or a second set of signals having a distinct number of channels from the first set of signals, and/or the like as input correlated to a plurality of labeled classes e.g., 12-channel configuration as output.

Still referring to FIG. 4, in some cases, one or more generative machine learning models may include generative adversarial network (GAN). As used in this disclosure, a "generative adversarial network" is a type of artificial neural network with at least two sub models (e.g., neural networks), a generator, and a discriminator, that compete against each other in a process that ultimately results in the generator learning to generate new data samples, wherein the "generator" is a component of the GAN that learns to create hypothetical data by incorporating feedbacks from the "discriminator" configured to distinguish real data from the hypothetical data. In some cases, generator may learn to make discriminator classify its output as real. In an embodiment, discriminator may include a supervised machine learning model while generator may include an unsupervised machine learning model as described in further detail below with reference to FIG. 4.

With continued reference to FIG. 4, in an embodiment, discriminator may include one or more discriminative models, i.e., models of conditional probability P(Y|X=x) of target variable Y, given observed variable X. In an embodiment, discriminative models may learn boundaries between classes or labels in given training data. In a non-limiting example, discriminator may include one or more classifiers as described in further detail below with continued reference to FIG. 4 to distinguish between different categories e.g., real vs. fake, or states e.g., TRUE vs. FALSE within the context of generated data such as, without limitations, a converted set of signals having the first number of channels, and/or the like. In some cases, computing device may implement one or more classification algorithms such as, without limitation, Support Vector Machines (SVM), Logistic Regression, Decision Trees, and/or the like to define decision boundaries.

In a non-limiting example, and still referring to FIG. 4, generator of GAN may be responsible for creating synthetic data that resembles real a converted set of signals having the first number of channels. In some cases, GAN may be configured to receive a first set of signals having a number of channels such as, without limitation, 6-lead ECG readings and/or 12-lead ECG readings, as input and generates corresponding converted set of signals having the first number of channels containing information describing or evaluating the performance of one or more sets of signals. On the other hand, discriminator of GAN may evaluate the authenticity of the generated content by comparing it to real sets of signals having the same number of channels as the first set of signals, for example, discriminator may distinguish between genuine and generated content and providing feedback to generator to improve the model performance.

With continued reference to FIG. 4, in other embodiments, one or more generative models may also include a variational autoencoder (VAE). As used in this disclosure, a "variational autoencoder" is an autoencoder (i.e., an artificial neural network architecture) whose encoding distribution is regularized during the model training process in order to ensure that its latent space includes desired properties allowing new data sample generation. In an embodiment, VAE may include a prior and noise distribution respectively, trained using expectation-maximization meta-algorithms such as, without limitation, probabilistic PCA, sparse coding, among others. In a non-limiting example, VEA may use a neural network as an amortized approach to jointly optimize across input data and output a plurality of parameters for corresponding variational distribution as it maps from a known input space to a low-dimensional latent space. Additionally, or alternatively, VAE may include a second neural network, for example, and without limitation, a decoder, wherein the "decoder" is configured to map from the latent space to the input space.

In a non-limiting example, and still referring to FIG. X, VAE may be used by computing device to model complex relationships between a first set of signals having a number of channels and a second set of signals having a distinct number of channels from the first number of channels e.g., 6-channel configuration and/or 12-channel configuration. In some cases, VAE may encode input data into a latent space, capturing a third set of signals having the second number of channels and/or a converted signal set having the first number of channels. Such encoding process may include learning one or more probabilistic mappings from observed first sets of signals having a number of channels and/or a second set of signals having a distinct number of channels from the first set of signals to a lower-dimensional latent representation. Latent representation may then be decoded back into the original data space, therefore reconstructing the first set of signals having a number of channels and/or a second set of signals having a distinct number of channels from the first set of signals. In some cases, such decoding process may allow VAE to generate new examples or variations that are consistent with the learned distributions.

With continued reference to FIG. 4, in some embodiments, one or more generative machine learning models may be trained on a plurality of channel data as described herein, wherein the plurality of channel data may provide visual information that generative machine learning models analyze to understand the dynamics of graphical waves and/or other channel data. Additionally, or alternatively, one or more generative machine learning models may utilize one or more predefined templates representing, for example, and without limitation, correct converted signal sets having the first number of channels. In a non-limiting example, one or more conversion tables (i.e., predefined models or representations of correct and ideal converted signal sets having the first number of channels) may serve as benchmarks for comparing and evaluating plurality of a first set of signals having a number of channels and/or a second set of signals having a distinct number of channels from the first set of signals.

Still referring to FIG. 4, computing device may configure generative machine learning models to analyze input data such as, without limitation, a first set of signals having a number of channels and/or a second set of signals having a distinct number of channels from the first set of signals to one or more predefined templates such as a conversion table representing correct a third set of signals having the second number of channels and/or converted signals having the first number of channels described above, thereby allowing computing device to identify discrepancies or deviations from converted signals set having the first number of channels. In some cases, computing device may be configured to pinpoint specific errors in a first set of signals having a number of channels and/or a second set of signals having a distinct number of channels from the first set of signals or any other aspects of the input data as described within this disclosure. In a non-limiting example, computing device may be configured to implement generative machine learning models to incorporate additional models to detect additional data if any. In some cases, errors may be classified into different categories or severity levels. In a non-limiting example, some errors may be considered minor, and generative machine learning model such as, without limitation, GAN may be configured to generate a third set of signals having the second number of channels and/or converted signal set having the first number of channels and contain only slight adjustments while others may be more significant and demand more substantial corrections. In some embodiments, computing device may be configured to flag or highlight errors in input data, altering the user to areas that need attention, directly on the sets of signals using one or more generative machine learning models described herein. In some cases, one or more generative machine learning models may be configured to generate and output indicators such as, without limitation, visual indicator, audio indicator, and/or any other indicators as described above. Such indicators may be used to signal the detected error described herein.

Still referring to FIG. 4, in some cases, computing device may be configured to identify and rank detected common deficiencies across plurality of data sources; for instance, and without limitation, one or more machine learning models may classify errors in a specific order e.g., missing channel data in a descending order of commonality. Such ranking process may enable prioritization of most prevalent issues, allowing instructors or computing device to address the issue or deficiencies.

Still referring to FIG. 4, in some cases, one or more generative machine learning models may also be applied by computing device to edit, modify, or otherwise manipulate existing data or data structures. In an embodiment, output of training data used to train one or more generative machine learning models such as GAN as described herein may include correlating a first set of signals having a number of channels with a second set of signals having a distinct number of channels from the first set of signals that linguistically or visually demonstrate modified signal sets e.g., conversion of a 6-channel signal set to a 12-channel signal set, and/or the like. In some cases, converted signal sets having the first number of channels may be synchronized with a first set of signals having a number of channels and/or a second set of signals having a distinct number of channels from the first number of channels. Additionally, or alternatively, converted signal sets may be generated using generative machine learning models to address the example issue or deficiency in an alternative way. In some cases, such converted signal sets may be integrated with the first set of signals having a number of channels, a second set of signals having a distinct number of channels from the first set of signals, and/or a third set of signals having the second number of channels, offering user a multisensory instructional experience.

Additionally, or alternatively, and still referring to FIG. 4, computing device may be configured to continuously monitor a first set of signals having a number of channel and/or a second set of signals having a distinct number of channels from the first set of signals. In an embodiment, computing device may configure discriminator to provide ongoing feedback and further corrections as needed to subsequent input data (e.g., signal sets with a number of channels). In some cases, one or more sensors such as, without limitation, wearable device, motion sensor, or other sensors or devices described herein may provide additional input data that may be used as subsequent input data or training data for one or more generative machine learning models described herein. An iterative feedback loop may be created as computing device continuously receive real-time data, identify errors as a function of real-time data, delivering corrections based on the identified errors, and monitoring user response and/or the like on the delivered corrections. In an embodiment, computing device may be configured to retrain one or more generative machine learning models based on converted signal sets or update training data of one or more generative machine learning models by integrating converted signal sets into the original training data. In such embodiment, iterative feedback loop may allow machine learning module to adapt to the user's needs and performance, enabling one or more generative machine learning models described herein to learn and update based on converted signal sets and generated feedback.

With continued reference to FIG. 4, other exemplary embodiments of generative machine learning models may include, without limitation, long short-term memory networks (LSTMs), (generative pre-trained) transformer (GPT) models, mixture density networks (MDN), and/or the like. As an ordinary person skilled in the art, upon reviewing the entirety of this disclosure, will be aware of various generative machine learning models may be used to output converted signal sets containing channel data that may include graphical images.

Still referring to FIG. 4, in a further non-limiting embodiment, machine learning module may be further configured to generate a multi-model neural network that combines various neural network architectures described herein. In a non-limiting example, multi-model neural network may combine LSTM for time-series analysis with GPT models for natural language processing. Such fusion may be applied by computing device to generate a third set of signals having the second number of channels and/or a converted signal set having the first number of channels. In some cases, multi-model neural network may also include a hierarchical multi-model neural network, wherein the hierarchical multi-model neural network may involve a plurality of layers of integration; for instance, and without limitation, different models may be combined at various stages of the network. Convolutional neural network (CNN) may be used for image feature extraction, followed by LSTMs for sequential pattern recognition, and a MDN at the end for probabilistic modeling. Other exemplary embodiments of multi-model neural network may include, without limitation, ensemble-based multi-model neural network, cross-modal fusion, adaptive multi-model network, among others. As an ordinary person skilled in the art, upon reviewing the entirety of this disclosure, will be aware of various generative machine learning models may be used to output converted signal sets containing channel data that may include graphical images described herein. As an ordinary person skilled in the art, upon reviewing the entirety of this disclosure, will be aware of various multi-model neural network and combination thereof that may be implemented by apparatus 100 in consistent with this disclosure.

Still referring to FIG. 4, machine-learning module 400 may be configured to perform a lazy-learning process 420 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 404. Heuristic may include selecting some number of highest-ranking associations and/or training data 404 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 4, machine-learning processes as described in this disclosure may be used to generate machine-learning models 424. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 424 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 424 may be generated by creating an artificial neural network, such as a convolutional neural network comprising an input layer of nodes, one or more intermediate layers, and an output layer of nodes. Connections between nodes may be created via the process of "training" the network, in which elements from a training data 404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 4, machine-learning algorithms may include at least a supervised machine-learning process 428. At least a supervised machine-learning process 428, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include inputs as described above as inputs, outputs described above as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 404. Persons skilled in the art, upon reviewing the entirety of this disclosure, will be aware of various possible variations of at least a supervised machine-learning process 428 that may be used to determine relation between inputs and outputs. Supervised machine-learning processes may include classification algorithms as defined above.

With further reference to FIG. 4, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 4, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 4, machine learning processes may include at least an unsupervised machine-learning processes 432. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 432 may not require a response variable; unsupervised processes 432 may be used to find interesting patterns and/or inferences between variables, to determine a degree of correlation between two or more variables, or the like.

Still referring to FIG. 4, machine-learning module 400 may be designed and configured to create a machine-learning model 424 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 4, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 4, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 4, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 4, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 4, one or more processes or algorithms described above may be performed by at least a dedicated hardware unit 436. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 436 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 436 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 436 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 5:
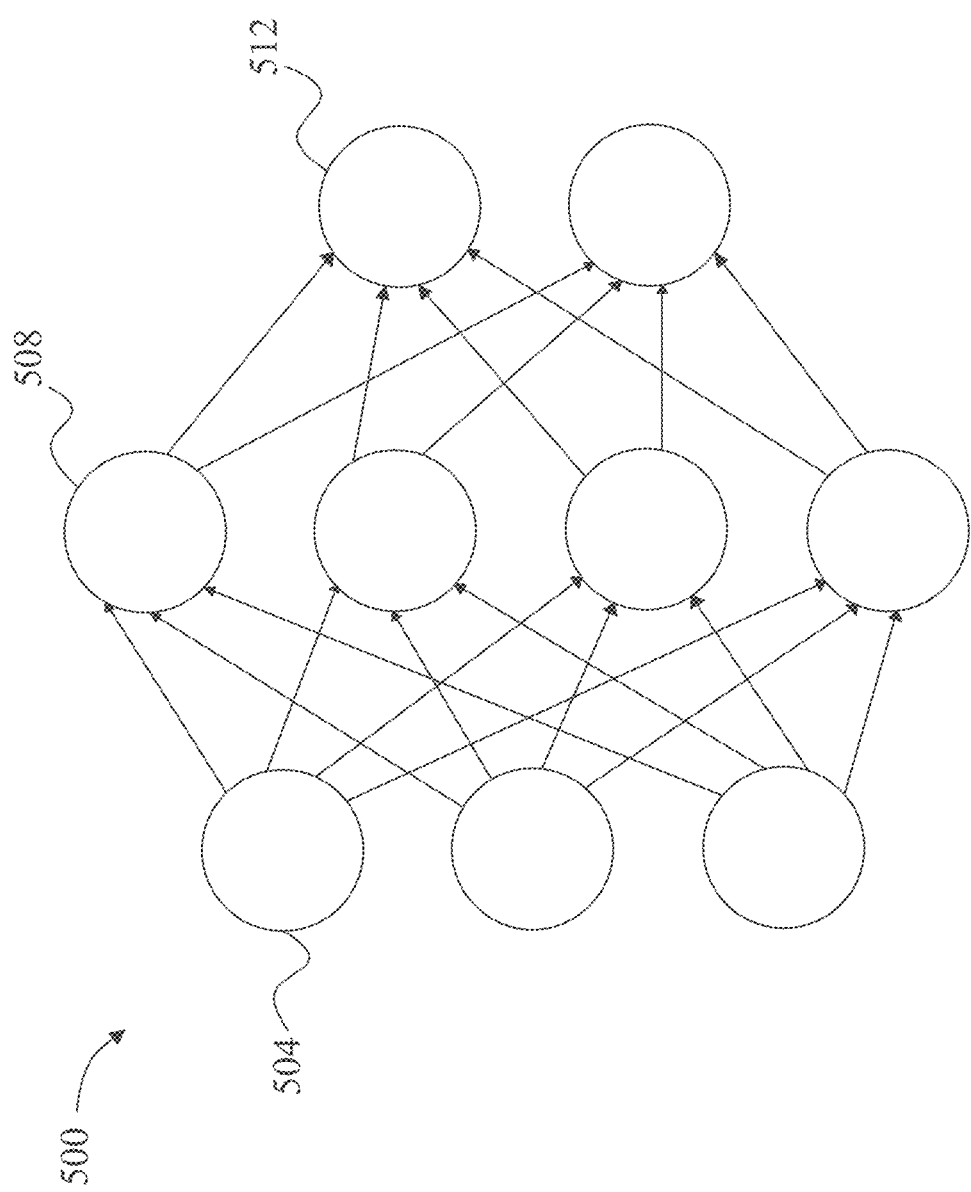
FIG. 5 is an exemplary neural network.

Referring now to FIG. 5, an exemplary embodiment of neural network 500 is illustrated. A neural network 500 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 504, one or more intermediate layers 508, and an output layer of nodes 512. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 6:
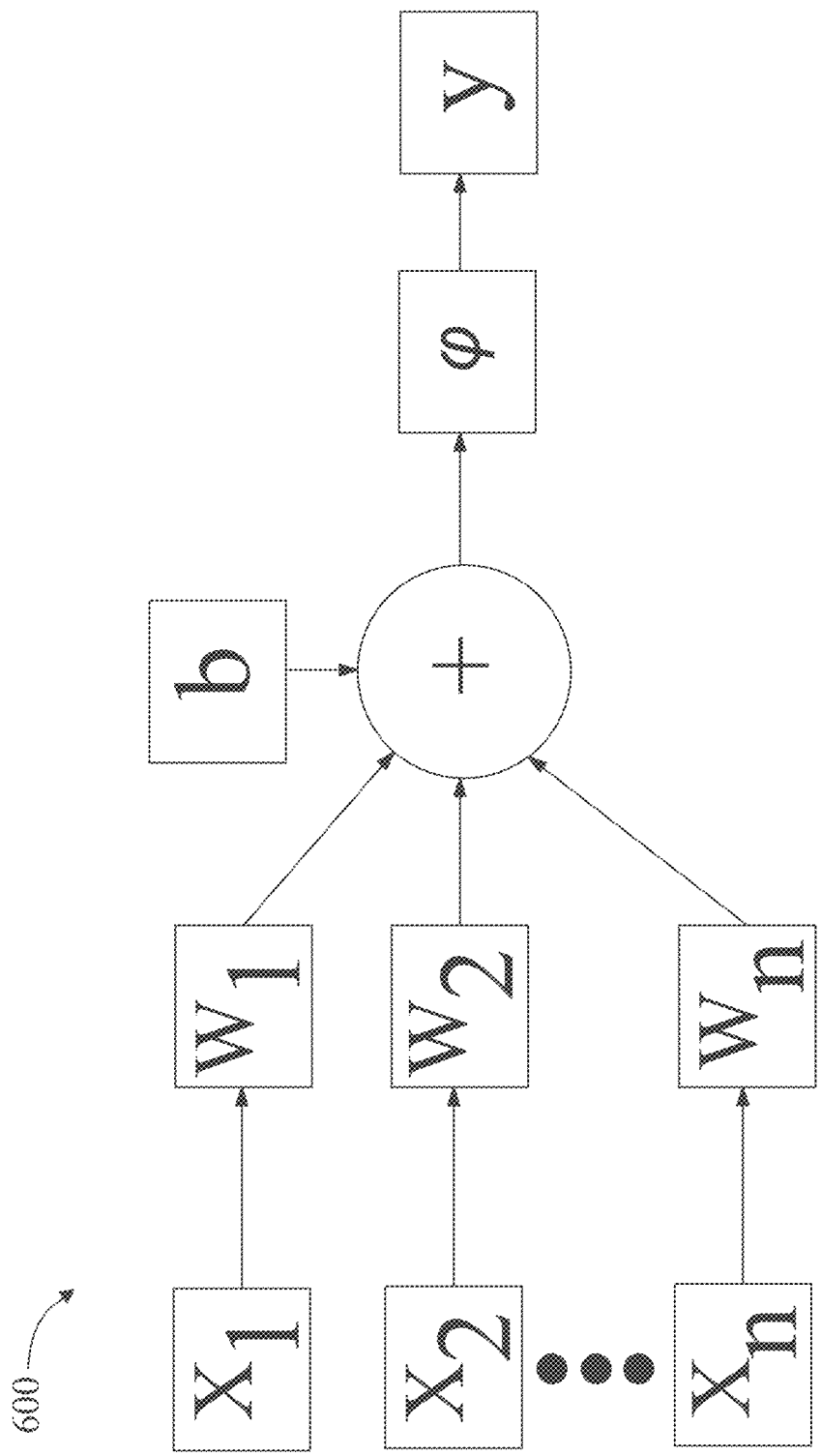
FIG. 6 is an exemplary node of a neural network.

Referring now to FIG. 6, an exemplary embodiment of a node 600 of a neural network is illustrated. A node may include, without limitation a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x & \text{for } x \geq 0 \\ \alpha(e^x - 1) & \text{for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
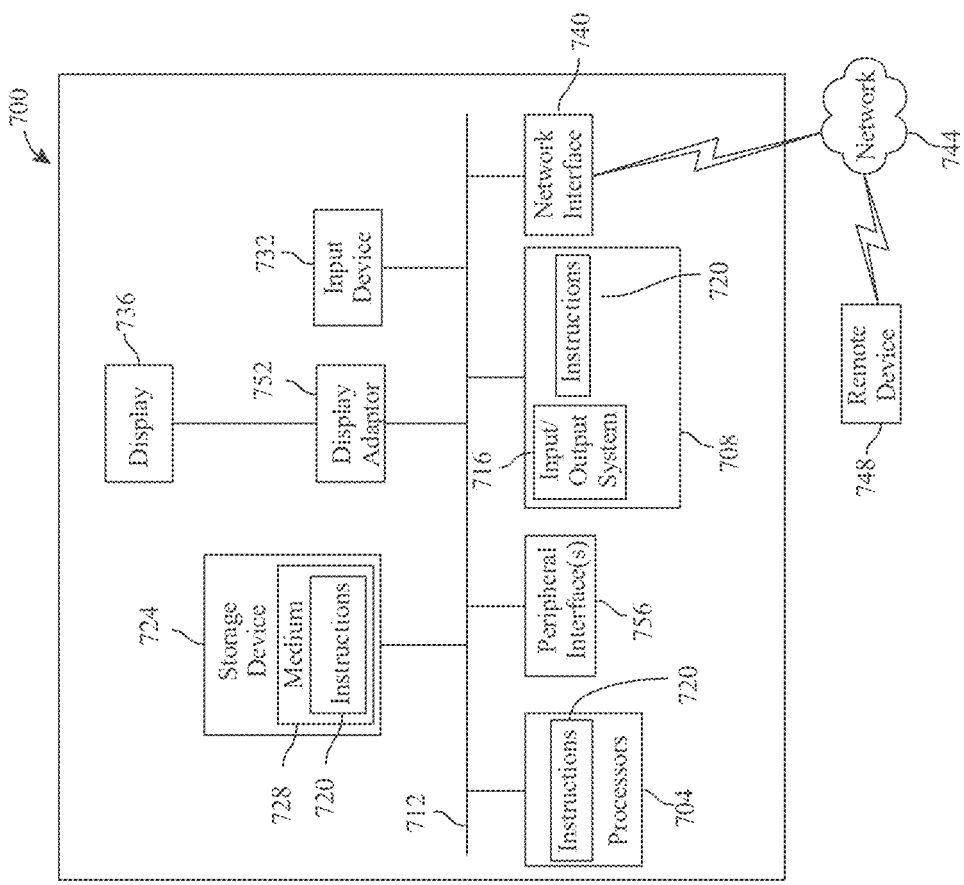
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display 736. Examples of a display device include, but are not limited to, a liquid crystal display (LCD), a cathode ray tube (CRT), a plasma display, a light emitting diode (LED) display, and any combinations thereof. Display adapter 752 and display 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for training a machine-learning model to generate determinations using mismatched-channel signals, wherein the apparatus comprises:
   at least a processor; and
   a memory communicatively connected to the at least a processor, wherein the memory contains instructions configuring the at least a processor to:
      receive a first set of signals comprising a first number of channels;
      process the first set of signals to simulate a second set of signals from a second number of channels that is distinct from the first number of channels,
         wherein processing the first set of signals comprises:
            filtering the first set of signals as a function of a preconfigured channel variation; and
            transforming the filtered first set of signals into the second set of signals;
      generate determinations from mismatched-channel signals using a trained signal conversion model, wherein the trained signal conversion model is trained using the filtered and transformed first set of signals and the second set of signals, wherein training the signal conversion model further comprises:
generating training data by correlating the filtered first set of signals and the second set of signals mimicking lower-channel configurations;
training the signal conversion model using the generated training data, wherein the training comprises utilizing a deep neural network comprises adjacent layers of nodes, and wherein the layers of nodes are iteratively updated;
deploying the trained signal conversion model;
generating new training data for the signal conversion model based on feedback from the deployment of the trained signal conversion model, and wherein the feedback is comprised of a comparison of the exemplary output data to desired output data; and
retraining the signal conversion model using the new training data;
receive a third set of signals having the second number of channels; and
output a set of converted signals having the first number of channels using the third set of signals and the trained signal conversion model.

2. The apparatus of claim 1, wherein the memory further contains instructions configuring the at least a processor to:
generate a visual representation of the set of converted signals; and
display the visual representation of the set of converted signals alongside a visual representation of the first set of signals using a visual interface at a display device.

3. The apparatus of claim 1, wherein the first set of signals comprises electrocardiogram signals.

4. The apparatus of claim 1, wherein the second number of channels comprises a reduced-channel configuration in comparison to the first set of signals.

5. The apparatus of claim 1, wherein the second number of channels comprises an increased-channel configuration in comparison to the first set of signals.

6. The apparatus of claim 1, wherein filtering the first set of signals as a function of a preconfigured channel variation comprises:
isolating one or more signals corresponding to the preconfigured channel variation from the first set of signals using a digital signal processing algorithm.

7. The apparatus of claim 1, wherein:
the second number of channels further comprises an increased-channel configuration; and
processing the first set of signals further comprises:
generating one or more synthetic signals as a function of the first set of signals to simulate one or more additional channels not presented in the first set of signals; and
generating the second set of signals representative of the increased-channel configuration by integrating the one or more synthetic signals with the first set of signals.

8. The apparatus of claim 1, wherein the signal conversion model comprises a deep neural network.

9. The apparatus of claim 1, wherein:
outputting the set of converted signals comprises outputting the set of converted signals in a target channel configuration; and
the memory contains instructions further configuring the processor to receive the target channel configuration from a user.

10. The apparatus of claim 9, wherein outputting the set of converted signals comprises outputting the set of converted signals into an additional machine-learning model, wherein the additional machine-learning model is trained to perform one or more specific diagnostic tasks using signals in the target channel configuration as input.

11. A method for training a machine-learning model to generate determinations using mismatched-channel signals, wherein the method comprises:
receiving, using at least a processor, a first set of signals comprising a first number of channels;
processing, using the at least a processor, the first set of signals to simulate a second set of signals from a second number of channels that is distinct from the first number of channels, wherein processing the first set of signals comprises:
filtering the first set of signals as a function of a preconfigured channel variation; and
transforming the filtered first set of signals into the second set of signals;
generating using the at least a processor, determinations from mismatched-channel signals using a trained signal conversion model, wherein the trained signal conversion model is trained using the filtered and transformed first set of signals and the second set of signals, and wherein training the signal conversion model further comprises:
generating training data by correlating the filtered first set of signals and the second set of signals mimicking lower-channel configurations;
training the signal conversion model using the generated training data, wherein the training comprises utilizing a deep neural network comprises adjacent layers of nodes, and wherein the layers of nodes are iteratively updated;
deploying the trained signal conversion model;
generating new training data for the signal conversion model based on feedback from the deployment of the trained signal conversion model, and wherein the feedback is comprised of a comparison of the exemplary output data to desired output data; and
retraining the signal conversion model using the new training data;
training, using the at least a processor, a signal conversion model using the filtered and
transformed first set of signals and the second set of signals;
receiving, using the at least a processor, a third set of signals having the second number of channels; and
outputting, using the at least a processor, a set of converted signals having the first number of channels using the third set of signals and the trained signal conversion model.

12. The method of claim 11, wherein the method further comprises:
generating, using the at least a processor, a visual representation of the set of converted signals; and
displaying, using the at least a processor, the visual representation of the set of converted signals alongside a visual representation of the first set of signals using a visual interface at a display device.

13. The method of claim 11, wherein the first set of signals comprises electrocardiogram signals.

14. The method of claim 11, wherein the second number of channels comprises a reduced-channel configuration in comparison to the first set of signals.

15. The method of claim 11, wherein the second number of channels comprises an increased-channel configuration in comparison to the first set of signals.

16. The method of claim 11, wherein filtering the first set of signals as a function of a preconfigured channel variation comprises:
   isolating one or more signals corresponding to the preconfigured channel variation from the first set of signals using a digital signal processing algorithm.

17. The method of claim 11, wherein:
   the second number of channels further comprises an increased-channel configuration; and
   processing the first set of signals further comprises:
      generating one or more synthetic signals as a function of the first set of signals to simulate one or more additional channels not presented in the first set of signals; and
      generating the second set of signals representative of the increased-channel configuration by integrating the one or more synthetic signals with the first set of signals.

18. The method of claim 11, wherein the signal conversion model comprises a deep neural network.

19. The method of claim 11, wherein:
   outputting the set of converted signals comprises outputting the set of converted signals in a target channel configuration; and
   the method further comprises receiving, by the at least a processor, the target channel configuration from a user.

20. The method of claim 19, wherein outputting the set of converted signals comprises outputting the set of converted signals into an additional machine-learning model, wherein the additional machine-learning model is trained to perform one or more specific diagnostic tasks using signals in the target channel configuration as input.

* * * * *